US 12,221,265 B2

(12) United States Patent
Kuruma et al.

(10) Patent No.: US 12,221,265 B2
(45) Date of Patent: Feb. 11, 2025

(54) HOLDING TOOL (71) Applicant: TERUMO KABUSHIKI KAISHA, Tokyo (JP)

(72) Inventors: Yosuke Kuruma, Kanagawa (JP); Kenta Mizumoto, Kanagawa (JP); Toshikazu Takeuchi, Kanagawa (JP); Ryohei Takeuchi, Kanagawa (JP)

(73) Assignee: TERUMO KABUSHIKI KAISHA, Tokyo (JP)

( * ) Notice: Subject to any disclaimer, the term of this patent is extended or adjusted under 35 U.S.C. 154(b) by 826 days.

(21) Appl. No.: 17/348,158

(22) Filed: Jun. 15, 2021

(65) Prior Publication Data
US 2021/0309438 A1    Oct. 7, 2021

Related U.S. Application Data

(63) Continuation of application No. PCT/JP2019/049530, filed on Dec. 18, 2019.

(30) Foreign Application Priority Data

Dec. 18, 2018  (JP) .................................. 2018-236020

(51) Int. Cl.
  *A01N 1/02* (2006.01)
  *B25J 15/00* (2006.01)
  *B65D 43/02* (2006.01)
  *B65D 81/24* (2006.01)

(52) U.S. Cl.
  CPC ......... *B65D 81/24* (2013.01); *B65D 43/0225* (2013.01); *B65D 2543/00018* (2013.01)

(58) Field of Classification Search
None
See application file for complete search history.

(56) References Cited

U.S. PATENT DOCUMENTS 6,286,684 B1   9/2001   Brooks et al.
10,370,631 B2  8/2019   Sugiura
(Continued)

FOREIGN PATENT DOCUMENTS

CN    105579569 A    5/2016
CN    106244415 A    12/2016
(Continued)

OTHER PUBLICATIONS

Office Action (Notice of Reasons for Refusal) issued Aug. 18, 2023, by the Japan Patent Office in corresponding Japanese Patent Application No. 2020-561484 and an English translation of the Office Action. (12 pages).
(Continued)

*Primary Examiner* — P. Kathryn Wright
(74) *Attorney, Agent, or Firm* — BUCHANAN INGERSOLL & ROONEY PC (57) ABSTRACT

A holding tool is configured to be used together with a container and a lid for the container to sandwich the container and the lid. The holding tool includes a base on which the container is placed, and a cover configured to cover the lid. The base and the cover each have an opening at a central portion and are configured to engage with each other to press and sandwich the container and the lid upward and downward.

26 Claims, 2 Drawing Sheets

(56) References Cited

U.S. PATENT DOCUMENTS

| | | | |
|---|---|---|---|
| 2003/0086830 A1* | 5/2003 | Haywood | B01L 3/502 422/547 |
| 2006/0240549 A1 | 10/2006 | Minton | |
| 2007/0166819 A1 | 7/2007 | Ghosh et al. | |
| 2009/0104699 A1* | 4/2009 | Newby | B01L 3/502 435/395 |
| 2015/0231628 A1 | 8/2015 | Nozaki et al. | |
| 2018/0177181 A1 | 6/2018 | Katou et al. | |
| 2020/0307889 A1 | 10/2020 | Tekeuchi et al. | |
| 2021/0309438 A1 | 10/2021 | Kuruma et al. | |

FOREIGN PATENT DOCUMENTS

| | | |
|---|---|---|
| CN | 106701577 A | 5/2017 |
| EP | 2 896 685 A1 | 7/2015 |
| JP | H09187271 A | 7/1997 |
| JP | 2007119033 A | 5/2007 |
| JP | 2009-523417 A | 6/2009 |
| JP | 2012130311 A | 7/2012 |
| JP | 2013039103 A | 2/2013 |
| JP | 2013-128457 A | 7/2013 |
| JP | 2015002717 A | 1/2015 |
| JP | 2016-220658 A | 12/2016 |
| JP | 2017063618 A | 4/2017 |
| JP | 2023101552 A | 7/2023 |
| WO | 2013176106 A1 | 11/2013 |
| WO | 2014041593 A1 | 3/2014 |
| WO | 2016/208018 A1 | 12/2016 |
| WO | 2016203018 A1 | 12/2016 |
| WO | 2019/017466 A1 | 1/2019 |
| WO | 2019/082261 A1 | 5/2019 |

OTHER PUBLICATIONS

Office Action issued Mar. 22, 2023, by the Intellectual Property Office of Singapore in corresponding Singapore Patent Application No. 11202105134V. (7 pages).

English translation of the Office Action (The Second Office Action) issued Oct. 16, 2023, by the National Intellectual Property Administration, P. R. China in corresponding Chinese Patent Application No. 201980075488.5. (12 pages).

Office Action (The First Office Action) issued Mar. 24, 2023, by the National Intellectual Property Administration, P. R. China in corresponding Chinese Patent Application No. 201980075488.5. (8 pages).

International Search Report (PCT/ISA/210) with translation and Written Opinion (PCT/ISA/237) mailed on Mar. 3, 2020, by the Japanese Patent Office as the International Searching Authority for International Application No. PCT/JP2019/049530.

Office Action (Notice of Reasons for Refusal) issued Feb. 2, 2023, by the Japan Patent Office in corresponding Japanese Patent Application No. 2020-561484, and an English translation of the Office Action. (10 pages).

English translation of the Office Action (Notice of Reasons for Refusal) issued on May 15, 2024, in corresponding Japanese Patent Application No. 2023-080577. (8 pages).

English translation of Office Action (Notice of Reasons for Refusal) issued on Oct. 3, 2024, in divisional patent application based on corresponding Japanese Patent Application No. 2020-561484. (6 pages).

* cited by examiner

HOLDING TOOL

CROSS-REFERENCES TO RELATED APPLICATIONS

This application is a continuation of International Application No. PCT/JP2019/049530 filed on Dec. 18, 2019, which claims priority to Japanese Patent Application No. 2018-236020 filed on Dec. 18, 2018, the entire content of both of which is incorporated herein by reference.

TECHNICAL FIELD

The present invention generally relates to a holding tool and a method.

BACKGROUND DISCUSSION

In recent years, new regenerative healthcare is being developed as a solution for severe heart failure. For example, there is a new approach to severe cardiac infarction or the like based on tissue engineering. In the new approach, a sheet cell culture prepared with a temperature-responsive culture dish is applied to a heart surface. The technique using a sheet cell culture enables safe transplantation of a large amount of cells over a wide range and is particularly useful for treatment of cardiac diseases (such as heart failure, particularly, chronic heart failure) associated with, for example, cardiac infarction (including chronic heart failure associated with cardiac infarction), dilated cardiomyopathy, ischemic cardiomyopathy, and systolic dysfunction (such as left ventricular systolic dysfunction).

For the clinical application of such a sheet cell culture, for example, the prepared sheet cell culture is stored in a container together with a preservative solution, and then, carried to an intensive care unit or the like where transplantation is to be performed. However, a sheet cell culture is low in absolute physical strength. Vibrations caused by carrying a container may wrinkle, break, or damage the sheet cell culture. For this reason, carrying a sheet cell culture requires highly-advanced techniques and extreme care.

In order to accommodate those needs, various methods and containers are being developed. For example, Japanese Patent Application Publication No. 2012-130311 (JP 2012-130311 A) discloses a container for storing and transporting a membrane tissue. In the container, a storage region is filled with a preservative solution to such an extent as not to form a gas layer, which makes it possible to prevent the preservative solution from rippling or flowing. Accordingly, the membrane tissue is prevented from being affected by vibrations and protected from damage. Furthermore, the container is designed to have a clip coupling mechanism that elastically presses a container body and a lid in order to facilitate the coupling between the container and the lid.

SUMMARY

However, in the clip mechanism, it is difficult to stably bring the lid and the container into close contact with each other.

The holding tool disclosed here is able to efficiently and reliably enable close contact between a container and a lid with a simple mechanism and a simple operation.

A holding tool is configured to be used together with a container and a lid for the container to sandwich the container and the lid. The holding tool comprises: a base configured to receive the container so that the container is positioned on the base, with the base including a central portion; a cover configured to cover the lid, with the cover including a central portion; the base including an opening at the central portion of the base; the cover including an opening at the central portion of the cover; and the cover and the base being configured to engage with each other while the container and the lid are positioned between the base and the cover to press and sandwich the container and the lid upward and downward.

The base may include an annular or semi-annular ridge configured to position the container relative to the base.

The base may also include an annular or semi-annular protruding wall configured to position the lid relative to the base.

The base may include a groove on a lower surface for preventing the base from sticking to a working surface.

The cover may be provided with a grip for grasping the cover.

The container and the lid may be made of a light transmissive material.

An elastic seal may be interposed between the container and the lid.

The subject to be stored in the container is a sheet cell culture.

A holding tool efficiently enables a close contact between a container and a lid with a simple mechanism and a simple operation and offers a great advantage in operability and manufacturing cost. In addition, since a subject inside the container can be observed from the outside, it is possible to easily check, for example, the state of the subject and whether foreign substances contaminate the subject. Furthermore, since relative positions between the container and the lid can be adjusted accurately, it is possible to enhance sealability. Particularly, interposing an elastic seal between the container and the lid further enhances the sealability because the seal can be pressed accurately.

By virtue of the holding tool, the container and the lid are reliably brought into close contact with each other and fixed. Accordingly, it is possible to prevent such problems that the lid comes off the container when being carried. Particularly, when the subject is a laminate of sheet cell cultures, the container can be carried with the inside reliably put into a liquid-tight state, and bubbles are prevented from entering the container, and the laminate is prevented from being displaced or damaged. Accordingly, while preventing deformation of the subject and maintaining a shape of the subject, it is possible to store the subject for a long period of time.

Another aspect involves a holding tool in combination with a device containing both a subject and a liquid in which the subject is immersed. The device comprises: a container and a lid engaged with one another and enclosing an interior containing the liquid and the subject that is immersed in the liquid. The holding tool comprises: a base and a cover, with the device being positioned on the base, and the base and the cover being engaged with each other to enclose an interior of the holding tool in which the device is located and to press the container and the lid from opposite ends towards each other. The cover includes a central portion and the base includes a central portion, and the central portion of the base or the central portion of the cover include an opening that permits a state of the liquid or the subject to be viewed.

Another aspect involves a method comprising: positioning a device on a base, wherein the device comprises a container and a lid engaged with one another and enclosing an interior, with the interior containing a liquid and a subject immersed in the liquid; engaging a cover with the base while the device is positioned on the base to enclose the device in an interior defined by the base and the cover such that the engaging of the cover with the base presses the container and the lid towards each other. The cover includes a central portion and the base including a central portion, and the central portion of the base or the central portion of the cover includes an opening that permits viewing of a state of the liquid or the subject in the device.

DETAILED DESCRIPTION

A fragile object herein represents an object that has a low physical strength and may be broken, damaged, or deformed by, for example, liquid vibration. Examples of the object include one provided with a thin portion, one having a band shape, and one having a sheet shape. The object having a sheet shape is not particularly limited and may be a sheet structure. Examples of the sheet structure include a flat membrane tissue including biologically derived materials such as a sheet cell culture and a film including various kinds of materials such as plastic, paper, woven fabric, non-woven fabric, metals, polymers, and lipids. Among these examples, preferred are objects that are persistent or hardly dissolved in a liquid. The sheet structure may be polygonal or circular and does not necessarily have a uniform width, thickness, diameter, and the like. The sheet structure to be used herein may be a single layer including one sheet or a laminate including two or more sheets. In the latter case, layers of the laminate may be, but are not necessarily, connected to each other. In a case where the layers are connected, overlapping parts may be connected thoroughly (completely) or partially. The term "fragile" herein indicates that an object is so vulnerable that it is difficult or substantially impossible to evaluate tensile properties of the object with, for example, a tensile testing machine in the related art (for example, one described in JIS K 7161) in which the object is fixed to a grasping tool outside a liquid. The fragile object, for example, shows a small value in each tensile property and has a difficulty in measuring tensile properties correctly with a tensile testing machine in the related art. Examples of the fragile object include those showing, in a tensile test, breaking loads of less than 10 N (Newton), less than 5 N, less than 2 N, less than 1 N, less than 0.5 N, less than 0.1 N, and less than 0.05 N. A minimum breaking load measured by a tensile test in the related art is typically about 1 N. For this reason, in an aspect of the disclosure here, it is preferable to use an object that shows a breaking load lower than 1 N (for example, less than 0.5 N) as the fragile object.

A graft herein refers to a biologically derived fragile object having a relatively low physical strength. The graft includes cultured cells (such as cell cultures) or harvested cells. The graft may also include products produced by cells. In addition to cells and/or products of cells, the graft may include materials (prostheses and supporting materials) that supplement and/or support a predetermined part (for example, an affected part) of a living body. The graft may have various kinds of shapes such as a sheet shape, a film shape, a lump shape, and a column shape. The graft is used for transplantation into a living body. Examples of the graft include three-dimensional cell tissues (such as an organoid and a spheroid) and two-dimensional cell tissues (such as a sheet cell culture).

The sheet cell culture herein has cells connected to each other to form a sheet. The cells may be connected to each other directly (or via a cellular element such as an adhesion molecule) and/or coupled to each other via an intervening substance. The intervening substance is not particularly limited as long as the substance connects cells at least physically (mechanically). An example of the intervening substance includes an extracellular matrix. The intervening substance is preferably derived from cells, particularly, cells that form a sheet cell culture. The cells are connected to each other at least physically (mechanically) but may be connected functionally, for example, chemically or electrically. The sheet cell culture may include one cell layer (a single-layered cell culture) or may include two or more cell layers (a multiple-layered cell culture). Furthermore, in the sheet cell culture, the cell does not necessarily have a clear layer structure and may have a three-dimensional structure with a thickness exceeding a thickness of one cell. For example, in a perpendicular cross section of the sheet cell culture, cells may be arranged unevenly (for example, in a mosaic manner) without being aligned evenly in the horizontal direction. The sheet cell culture may exist as an independent single (one) sheet cell culture or as a laminate having two or more independent single (one) sheet cell cultures being laminated. In the laminate, for example, two layers (two sheets), three layers (three sheets), four layers (four sheets), five layers (five sheets), or six layers (six sheets) of sheet cell cultures may be laminated.

The sheet cell culture herein includes any kind of cells that may form the aforementioned structures. Examples of the cells include, but are not limited to, adherent cells (adhesive cells). Examples of the adherent cells include adherent somatic cells (such as cardiac muscle cells, fibroblast cells, epithelial cells, endothelial cells, hepatic cells, pancreatic cells, renal cells, adrenal cells, periodontal ligament cells, gingival cells, periosteal cells, skin cells, synovial cells, and cartilage cells) and stem cells (for example, tissue stem cells such as myoblast cells and cardiac stem cells; pluripotent stem cells such as embryonic stem cells and induced pluripotent stem (iPS) cells; and mesenchymal stem cells). The somatic cells may be differentiated from stem cells, particularly, from iPS cells. Examples of the cells that may form the sheet cell culture include, but are not limited to, myoblast cells (such as skeletal myoblast cells), mesenchymal stem cells (such as cells derived from bone marrow, adipose tissue, peripheral blood, skin, hair roots, muscular tissue, endometrium, placenta, and cord blood), cardiac muscle cells, fibroblast cells, cardiac stem cells, embryonic stem cells, iPS cells, synovial cells, cartilage cells, epithelial cells (such as oral mucosal epithelial cells, retinal pigment epithelial cells, and nasal mucosal epithelial cells), endothelial cells (such as vascular endothelial cells), hepatic cells (such as hepatic parenchymal cells), pancreatic cells (such as islet cells), renal cells, adrenal cells, periodontal ligament cells, gingival cells, periosteal cells, and skin cells. Preferable examples herein are cells that form a single-layered cell culture such myoblast cells or cardiac muscle cells, and particularly preferable examples are skeletal myoblast cells or iPS cell-derived cardiac muscle cells.

The cells may be derived from any organism treatable with a cell culture. Examples of the organism include, but are not particularly limited to, humans, non-human primates, dogs, cats, pigs, horses, goats, and sheep. Furthermore, one type of cell or two or more types of cells may be used for forming a sheet cell culture. In a preferred aspect, when the number of cells that form a cell culture is two or more, a ratio (purity) of the greatest number of cells, for example, a ratio of skeletal myoblast cells, is 65% or more, preferably 70% or more, and more preferably 75% or more, at the end of producing the cell culture.

The sheet cell culture may be a sheet cultured tissue or the like obtained by inoculating and culturing cells in a scaffold (scaffold during cell culturing). However, the sheet cell culture is preferably composed of a material derived from cells that form a cell culture and does not include other materials.

The sheet cell culture may be produced by any known technique.

In an aspect of the disclosure here, the sheet cell culture is a sheet skeletal myoblast cell culture. The reason is that maintaining a shape of a sheet skeletal myoblast cell culture in a liquid is of great significance since a sheet skeletal myoblast cell culture is so fragile that the cell culture breaks by its own weight when a part of the cell culture is grabbed and that such fragility not only disables the cell culture to be carried independently but also makes it extremely difficult for the cell culture to return to the original shape when the cell culture is once folded.

A container herein is not specifically limited as long as the container houses a fragile object, a liquid, and the like and prevents leakage of the liquid. The container to be used herein may be of any type including a commercially available container. Examples of a material of the container include, but are not limited to, polyethylene, polypropylene, Teflon (registered trademark), polyethylene terephthalate, polymethyl methacrylate, nylon 6,6, polyvinyl alcohol, cellulose, silicon, polystyrene, glass, polyacrylamide, polydimethylacrylamide, and metals (such as iron, stainless steel, aluminum, copper, and brass). In addition, the container preferably has at least one flat bottom surface for maintaining a shape of the fragile object. Examples of the container include, but are not limited to, a petri dish, a cell culture dish, and a cell culture bottle. The flat bottom surface typically has an area of 9.1 to 78.5 $cm^2$, 1.13 to 78.5 $cm^2$, preferably 12.6 to 78.5 $cm^2$, and more preferably 9.1 to 60.8 $cm^2$, but is not limited thereto.

Herein, the liquid inside the container includes at least one component. Examples of the component include, but are not particularly limited to, water, aqueous solution, non-aqueous solution, suspension, and emulsion.

The solution or liquid herein may be of any type as long as the solution or liquid is a fluid having fluidity as a whole and may include solid substances such as cell scaffolds and other non-liquid components such as bubbles.

The component included in the liquid inside the container is not particularly limited as long as the component has little influence on the fragile object. In a case where the fragile object is a membrane including a biologically derived material, the component included in the liquid inside the container is preferably biocompatible from a viewpoint of biological stability and long-term storage. In other words, the component included in the liquid is preferably one that does not cause undesired effects such as inflammatory reactions, immune reactions, and intoxicating reactions against living tissue or cells or one that causes such effects to a small extent. Examples of the component include water, physiological saline, physiological buffers (such as HBSS, PBS, EBSS, Hepes, and sodium bicarbonate), media (such as DMEM, MEM, F12, DMEM/F12, DME, RPMI1640, MCDB, L15, SkBM, RITC80-7, and IMDM), carbohydrate solutions (such as sucrose solution and Ficoll-paque (registered trademark) PLUS), seawater, serum-containing solution, Renografin (registered trademark) solution, metrizamide solution, meglumine solution, glycerin, ethylene glycol, ammonia, benzene, toluene, acetone, ethyl alcohol, benzol, oil, mineral oil, animal fat, vegetable oil, olive oil, colloidal solution, liquid paraffin, turpentine oil, linseed oil, and castor oil.

In a case where the fragile object is a sheet cell culture, the component included in the liquid inside the container is preferably one that enables stable storage of cells and contains the minimal amount of oxygen and nutrients necessary for cell survival and does not break the cells due to osmotic pressure or the like. Examples of the component include, but are not limited to, physiological saline, physiological buffers (such as HBSS, PBS, EBSS, Hepes, and sodium bicarbonate), media (such as DMEM, MEM, F12, DMEM/F12, DME, RPMI1640, MCDB, L15, SkBM, RITC80-7, and IMDM), and carbohydrate solutions (such as sucrose solution and Ficoll-paque PLUS (registered trademark)).

The liquid inside the container is not particularly limited in amount as long as it is enough to hold the fragile object while a lid is attached to the container and the liquid volume between the bottom of the container and the lid is high enough to prevent the fragile object from vibrating in the liquid. That is, when a space is generated between the liquid level and the lid, the liquid waves (or liquid level fluctuates), and the fragile object easily vibrates in the liquid. Therefore, it is preferable to adjust the liquid volume so as not to generate a space between the liquid level and the lid. In an aspect of the disclosure here, the sheet cell culture has a diameter of about 35 to 55 mm and an area of 6 $cm^2$ or more or 10 $cm^2$ or more. The liquid volume may be, for example, 1.0 mm to 20.0 mm regardless of the diameter of the sheet cell culture.

The lid herein is not particularly limited as long as the lid seals the container. Examples of a material of the lid include, but are not limited to, polyethylene, polypropylene, Teflon (registered trademark), polyethylene terephthalate, polymethyl methacrylate, nylon 6,6, polyvinyl alcohol, cellulose, silicon, polystyrene, glass, polyacrylamide, polydimethylacrylamide, and metals (such as iron, stainless steel, aluminum, copper, and brass).

The lid and the container are not particularly limited in shape as long as the lid and the container engage with each other to create a sealed space. For example, in a case where the container is a general-purpose petri dish, the lid preferably has a circular shape. Furthermore, the lid and/or the container may include a light transmissive material to make it possible to check the state of the fragile object housed in the container and the presence or absence of bubbles in the liquid.

The fragile object herein is held in a liquid in a container containing the liquid. The fragile object in the liquid is not particularly limited in position, but the fragile object is disposed at a position where the lid and the fragile object are not in contact with each other (or may be in contact with each other) while the lid is attached to the container to form a sealed space. In the liquid of the container, the fragile object is preferably on or near the bottom surface of the container.

A seal herein refers to a member that is interposed between the container and the lid to improve sealability of the container. Examples of the seal include a packing ring.

The seal preferably includes an elastic material to absorb manufacturing tolerances of the container and the lid and to enhance the sealability of the container. Examples of the elastic material include, but are not limited to, natural rubber, elastomer, nitrile rubber, and silicon rubber.

Hereinafter, preferred embodiments of the holding tool will be described in detail with reference to the drawings.

Figure 1:
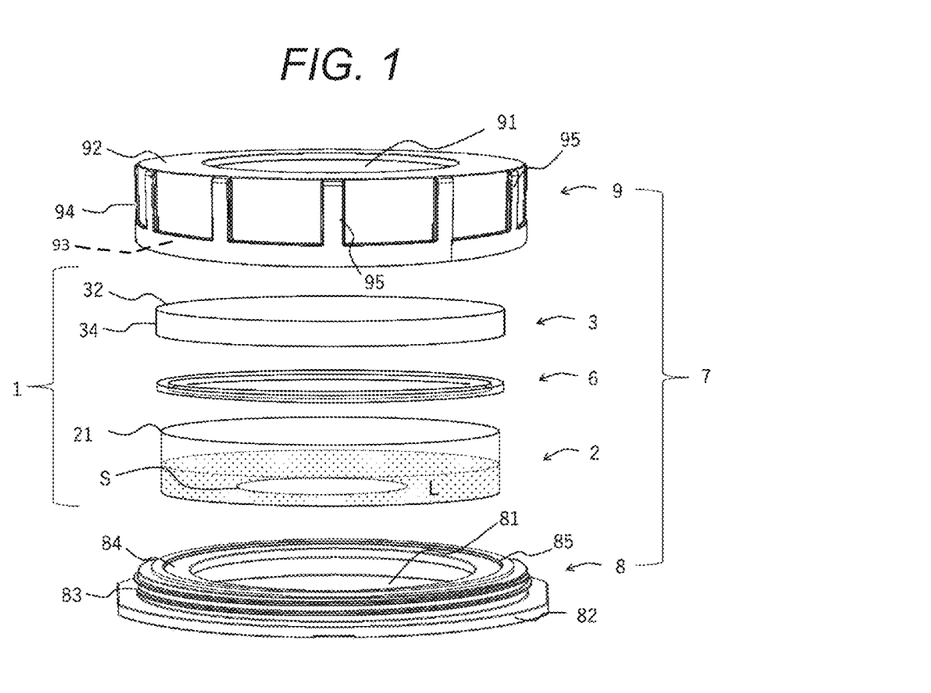
FIG. 1 is a perspective view of a holding tool according to a first embodiment.
Figure 2:
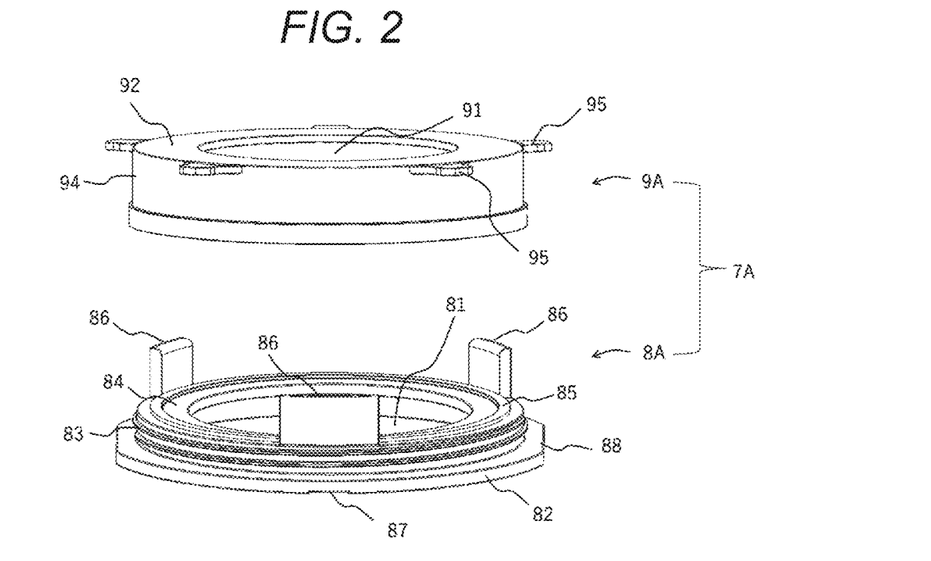
FIG. 2 is a perspective view of a holding tool according to a second embodiment.
Figure 3:
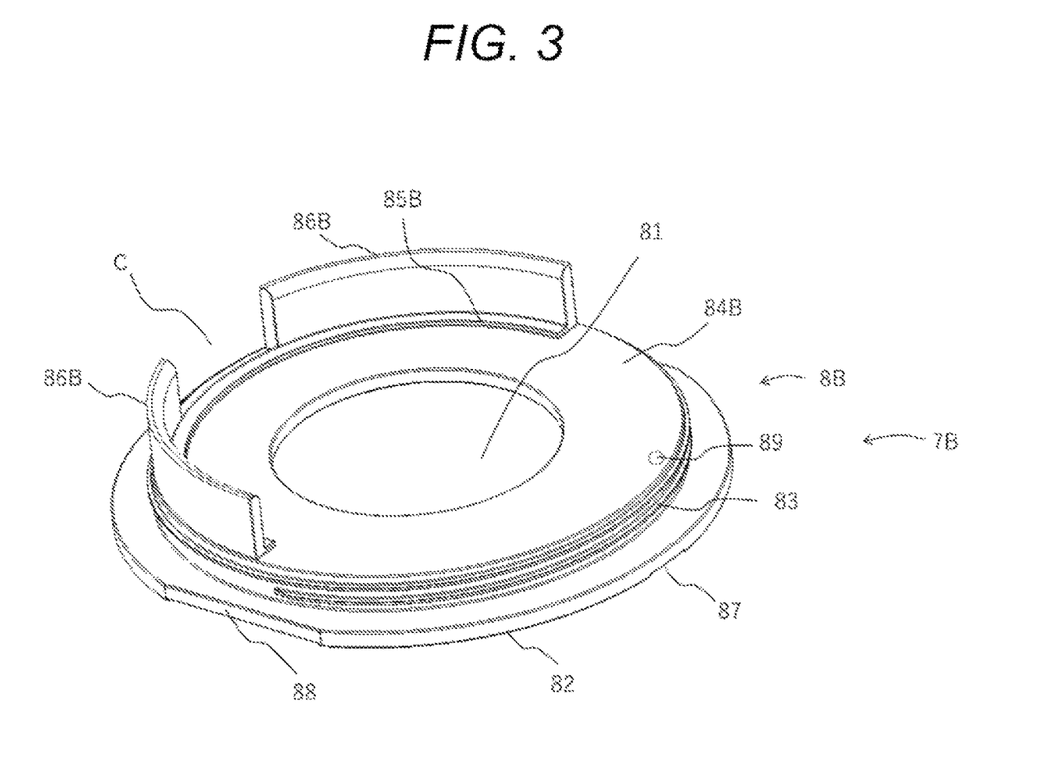
FIG. 3 is a perspective view of a holding tool according to a third embodiment.

FIG. 1 is a perspective view of a holding tool 7 according to a first embodiment. FIG. 2 is a perspective view of a holding tool 7A according to a second embodiment. FIG. 3 is a perspective view of a holding holding tool 7B according to a third embodiment. In each drawing in this application, for the purpose of illustration, sizes of the illustrated members are emphasized as appropriate and are different from the actual sizes.

First Embodiment

As illustrated in FIG. 1, a holding tool 7 according to this embodiment includes a base 8 and a cover 9. The holding tool 7 sandwiches a device 1 that includes a container 2 and a lid 3 for sealing the container 2 by pressing the device 1 upward and downward. The container 2 has a commercially available petri dish shape having a rim 21 surrounding an opening and forms a storage space for storing a subject S (for example, a fragile object). The lid 3 includes a top plate 32 and a cylindrical skirt wall 34 hanging down or projecting in the direction of the bottom of the container 2 from a peripheral edge of the top plate 32. The lid 3 engages with the container 2 to form a sealed space.

The base 8 and the cover 9 both have a circular shape and press the device 1 upward and downward in an appropriate manner. That is, the base 8 and the cover 9 press the container 2 and a lid 3 from opposite sides (in opposite directions) towards one another. The base 8 includes an opening 81, a bottom 82, a thread (engagement unit) 83, a stage 84, and an upstanding ridge 85. In this embodiment, the engagement refers to screwing. The stage 84 includes a stage surface or support surface on an upper surface where the container 2 is to be placed and an opening 81 in a central portion. The stage 84 includes the ridge 85 (elongated ridge) having an annular shape. When the container 2 is placed on the stage surface, the ridge 85 surrounds a lower end (bottom portion) of the container 2 and defines a position of the container 2 relative to the base 8. The stage 84 has a disk shape protruding upward from the bottom 82 and has a side peripheral surface provided with the thread 83. The bottom 82 has an outer diameter larger than that of the stage 84 and serves as a bottom when the base 8 is placed on a table or the like.

The cover 9 includes an opening 91, a top 92, a thread (engagement unit) 93, a cylindrical skirt wall 94, and grips 95. The top 92 includes a cover surface that covers an upper surface of the lid 3 and includes the opening 91 in a central portion. The top 92 includes the cylindrical skirt wall 94 hanging down from a peripheral edge of the top 92. The top 92, the cylindrical skirt wall 94, and the stage 84 surround the device 1 to sandwich the device 1. The thread 93 is disposed on the inner periphery of a lower end of the cylindrical skirt wall 94. The cover 9 is attached to the base 8 when the thread 93 is screwed with the thread 83 of the base 8. Optionally, an inner diameter of at least a part of the cylindrical skirt wall 94 (for example, the inner periphery of an upper end of the cylindrical skirt wall 94) may be matched with an outer diameter of the lid 3 so as to define a position of the lid 3 relative to the holding tool 7.

When the holding tool 7 is used, the lid 3 is put on the container 2 storing the subject S. At this time, optionally, the lid 3 may be put on the container 2 filled with a liquid L to form a liquid-tight space. Furthermore, optionally, a seal 6 may be interposed between the rim 21 of the container 2 and the top plate 32 of the lid 3, or another seal (not illustrated) may be interposed at a suitable position between the container 2 and the lid 3 so as to enhance the sealability. Next, the container 2 is placed on the base 8. At this time, the ridge 85 enables the container 2 to be positioned at the center of the stage 84. Since the thread 83 of the base 8 is disposed on the lower side of the stage 84, that is, the thread 83 does not have a structure surrounding the side surface of the container 2, it is possible to prevent vibration by sliding the container 2 in the lateral direction when placing the container 2 on the stage 84 or when removing the container 2 from the stage 84. Next, the cover 9 is attached to the base 8 so that the container 2/the lid 3 are enclosed in the interior of the holding tool 7. At this time, the cylindrical skirt wall 94 enables the lid 3 to be positioned at the center of the cover 9 (and the base 8).

In this manner, the holding tool 7 can define the relative positions between the container 2 and the lid 3 using the ridge 85 of the base 8 and the cylindrical skirt wall 94 of the cover 9. When sandwiching the device 1, the thread 83 of the base 8 and the thread 93 of the cover 9 are screwed together. At this time, the grips 95 provided as protrusions or raised parts (or may be grooves) on the outer periphery of the cylindrical skirt wall 94 are grasped for the screwing operation. Accordingly, the container 2 and the lid 3 are tightened with strong upward and downward forces. Such a configuration is versatile and suitable for use, for example, in a case where the container 2 has no thread like a general-purpose petri dish. Particularly, such a configuration offers an advantage when an elastic seal is interposed between the container 2 and the lid 3 because the seal is accurately compressed between the container 2 and the lid 3 having relative positions determined accurately and enhances the sealability. Since the cover 9 is screwed only by a height of the thread 83 of the base 8, not only the sandwiching operation is easy but also adjustment of sandwiching pressure is easy. Accordingly, it is possible to prevent destruction of the device 1.

Since the base 8 and the cover 9 respectively include the opening 81 and the opening 91 in the central portions, it is possible to constantly observe, for example, the fixed position of the device 1 and the state of the liquid L or the state of the subject S stored in the interior of the device 1 and immersed in the liquid L. Particularly, such a configuration offers an advantage when the container 2 and the lid 3 include a light transmissive material (i.e., when the container 2 and the lid 3 are made of a light transmissive material). The reason is that, even when the subject S is an object having low visibility like a sheet cell culture, when light is emitted from one opening, it is possible to observe the sheet cell culture from the other opening. Furthermore, in a case where a liquid-tight space is formed in the aforementioned manner, it is possible to press the lid 3 against the container 2 while checking, from the opening 91, whether bubbles or foreign matters contaminate the inside of the container 2. Next, the device 1 is carried. Since the device 1 is firmly sandwiched by the holding tool 7, it is possible to prevent such problems that the lid 3 comes off the container 2 due to shaking or the like during the carry. Furthermore, since the periphery is surrounded by the holding tool 7, the device 1 is protected from external shock. Finally, the holding tool 7 is removed from the device 1 at the destination, and the device 1 is used.

Although the holding tool disclosed here has been described with reference to the illustrated embodiments and variations, the present invention is not limited to the disclosed embodiments and variations. For example, the thread 83 on the base 3 and the thread 93 on the cover 9 may be replaced with other engagement mechanisms having a function of pressing the device 1 from the vertical direction such as a slide engagement (see, for example, JP 2006-315757 A), a flange fitting (see, for example, JP 2006-001582 A), and a protrusion engagement (see, for example, JP 2016-203985 A). The annular ridge 85 may be replaced by other structure such as a plurality of annularly arranged projections by which the container 2 is positioned on the stage surface. As the subject S, for example, a fragile object (such as a laminate of sheet cell cultures) may be stored. In this case, the container 2 is put into a liquid-tight state. Accordingly, it is possible to carry the fragile object while maintaining a shape of the fragile object.

Second Embodiment

Next, a second embodiment of the holding tool, representing another example of the inventive holding holding tool disclosed here, will be described. Hereinafter, differences from the first embodiment will be described in detail but a detailed description of features already described above will not be repeated.

As illustrated in FIG. 2, a holding tool 7A according to this embodiment includes a base 8A and a cover 9A. In this embodiment, the base 8A further includes protruding or upstanding walls 86, a groove 87, and a cutout portion 88. The protruding walls 86 are a plurality of circumferentially spaced-apart walls provided outside a ridge 85 and protruding higher than the container 2 from a stage 84. The groove 87 is disposed on a lower surface of a bottom 82 of the base 8A so as to prevent the base 8A from sticking to a working surface when the base 8A is placed on a table or the like.

When the holding tool 7A is used, the ridge 85 enables the container 2 to be positioned at the center of the base 8. Next, when the container 2 is covered by the lid 3, the lid 3 is put along the protruding walls 86 so as to be positioned at the center of the base 8. That is, an operator uses the ridge 85 and the protruding walls 86 of the base 8A to define relative positions between the container 2 and the lid 3 so that the lid 3 is properly positioned or located on the container 2. Particularly, such a configuration offers an advantage when an annular seal is interposed between the container 2 and the lid 3 because the seal can be pressed accurately.

Next, the device 1 is sandwiched. At this time, the screwing operation can be easily performed by grasping grips 95 or protrusions radially protruding from the cover 9A and the cutout portion 88 disposed on the side surface of the bottom 82 of the base 8A. When the device 1 is used, the cover 9A is unscrewed, and the device 1 is removed from the base 8A. At this time, it is easy to grasp the device 1 because the device 1 is exposed from a gap between the plurality of protruding walls 86. In addition, since the plurality of protruding walls 86 is arranged to surround the container 2, the lid 3 is accurately positioned relative to the container 2.

Third Embodiment

Next, a third embodiment of the holding tool, representing a further example of the inventive holding tool disclosed here, will be described. Hereinafter, differences from the first embodiment and the second embodiment will be described in detail but a detailed description of features already described above will not be repeated.

As illustrated in FIG. 3, a holding tool 7B according to this embodiment includes a cover and a base 8B. The base 8B includes a stage or support surface 84B, a ridge 85B, and a protruding or upstanding wall 86B (a detailed description of other features/configurations is not repeated). The ridge 85B is disposed on the stage 84B in a semi-annular shape. The protruding wall 86B is disposed in a semi-annular shape outside the ridge 85B and partially provided with a cutout (gap) C (two or more circumferentially spaced-apart protruding or upstanding walls 86B may be disposed in a semi-annular shape with a gap between the two). That is, in this embodiment, a half of the stage surface of the stage 84B (the opposite half of the ridge 85B and the protruding wall 86B) is a flat surface.

When the holding tool 7B is used, the container 2 is slid laterally (in a direction toward the ridge 85B and the protruding wall 86B) from the opposite side of the ridge 85B and the protruding wall 86B. At this time, sliding the container 2 on the flat surface of the stage 84B prevents inadvertent vibration of the container 2. Next, the lid 3 is attached to the container 2. At this time, the lid 3 is pressed against (contacts) the protruding wall 86B of the base 8B so as to be accurately positioned relative to the container 2. When the device 1 is used, the device 1 is removed from the base 8A. At this time, a side surface of the device 1 (the container 2 and/or the lid 3) exposed from the cutout C is pushed by virtue of the pressing force applied by the base and the cover. Accordingly, the device 1 is slid on the flat surface and removed. In order to make the sliding direction clear when the device 1 is slid on the base 8A, a projection 89 or a mark may be disposed on the stage 84B on the opposite side of the cutout C. With such a configuration, the device 1 is accurately positioned on the stage 84B only by sliding the device 1 between the projection 89 and the cutout C. Furthermore, the projection 89 is disposed facing the cutout C on the extension line of the ridge 85B, and the side surface of the device 1 is locked by the projection 89. Accordingly, it is possible to prevent displacement (lateral displacement) of the device 1.

As described above, the holding tool according to the first to third embodiments of the present application efficiently enables a close contact between a container and a lid with a simple mechanism and a simple operation and offers a great advantage in operability and manufacturing cost. In addition, since a subject inside the container can be observed from the outside, it is possible to easily check, for example, the state of the subject and whether foreign substances contaminate the subject. Furthermore, since relative positions between the container and the lid can be adjusted accurately, it is possible to enhance sealability. Particularly, interposing an elastic seal between the container and the lid further enhances the sealability because the seal can be pressed accurately.

In addition, with the holding tool disclosed here, the container and the lid are reliably brought into close contact with each other and fixed. Accordingly, it is possible to prevent such problems that the lid comes off the container when being carried. Particularly, when the subject is a laminate of sheet cell cultures, the container can be carried with the inside reliably put into a liquid-tight state, and bubbles are prevented from entering the container, and the laminate is prevented from being displaced or damaged. Accordingly, while preventing deformation of the subject and maintaining a shape of the subject, it is possible to store the subject for a long period of time.

The present invention is not limited to the embodiments. Those skilled in the art can appropriately combine the configurations and shapes of the holding tool according to the first to third embodiments to achieve a holding tool with different configurations and shapes. For example, the cover 9 or the cover 9A may be combined with the base 8, the base 8A, or the base 8B. Alternatively, the ridge 85, the ridge 85B, the protruding wall 86, or the protruding wall 86B may be combined with the base 8, the base 8A, or the base 8B.

In addition, each component may be replaced with any component that exhibits similar functions. Alternatively, any component may be added to each component.

The detailed description above describes embodiments of a holding tool and method representing examples of the inventive holding tool and method disclosed here. The invention is not limited, however, to the precise embodiments and variations described. Various changes, modifications and equivalents can be effected by one skilled in the art without departing from the spirit and scope of the invention as defined in the accompanying claims. It is expressly intended that all such changes, modifications and equivalents which fall within the scope of the claims are embraced by the claims.

What is claimed is:

1. A holding tool configured to be used together with a container and a lid for the container to sandwich the container and the lid, the holding tool comprising:
   a base configured to receive the container so that the container is positioned on the base, the base including a central portion;
   a cover configured to cover the lid, the cover including a central portion;
   the base including an opening at the central portion of the base;
   the cover including an opening at the central portion of the cover; and
   the cover and the base being configured to engage with each other while the container and the lid are positioned between the base and the cover to press and sandwich the container and the lid upward and downward; and
   the base including an annular or semi-annular protruding wall that protrudes upwardly away from the base, the protruding wall being configured to extend above the container when the container is positioned on the base to position the lid relative to the base; and
   the base including an annular or semi-annular ridge configured to position the container relative to the base, the annular or semi-annular protruding wall being positioned outside the annular or semi-annular ridge as seen in a plan view of the base.

2. The holding tool according to claim 1, wherein the annular or semi-annular protruding wall comprises a plurality of semi-annular protruding walls that protrude upwardly away from the base.

3. The holding tool according to claim 1, wherein the base includes a groove on a lower surface for preventing the base from sticking to a working surface.

4. The holding tool according to claim 1, wherein the cover includes a plurality of grips each projecting radially outwardly from the cover for grasping the cover, the grips being circumferentially spaced apart from one another so that a space exist between circumferentially adjacent grips.

5. The holding tool according to claim 1, wherein the container and the lid are made of a light transmissive material.

6. The holding tool according to claim 1, wherein the base includes an outer periphery provided with a screw thread.

7. The holding tool according to claim 1, wherein the cover includes an outer periphery, the outer periphery of the cover including a plurality of protrusions that are circumferentially spaced-apart from one another along the outer periphery of the cover.

8. The holding tool according to claim 1, wherein the annular or semi-annular protruding wall comprises a plurality of protruding walls that are spaced apart from one another in a circumferential direction so that a space exists between circumferentially adjacent protruding walls.

9. The holding tool according to claim 1, wherein the annular or semi-annular ridge has a semi-annular shape, the annular or semi-annular protruding wall comprising at least two protruding walls arranged in a semi-annular shape and spaced apart from one another so that a space exists between the two protruding walls, the base including a projection positioned opposite the space between the two protruding walls.

10. A holding tool in combination with a device containing both a subject and a liquid in which the subject is immersed,
    the device comprising:
        a container and a lid engaged with one another and enclosing an interior containing the liquid and the subject that is immersed in the liquid;
    the holding tool comprising:
        a base and a cover, the device being positioned on the base, the base and the cover being engaged with each other to enclose an interior of the holding tool in which the device is located and to press the container and the lid from opposite ends towards each other;
        the cover including a central portion and the base including a central portion;
        the central portion of the base or the central portion of the cover including an opening that permits a state of the liquid or the subject to be viewed; and
        the base including an annular or semi-annular protruding wall that protrudes away from the base and terminates in a free end positioned above the container to position the lid relative to the base; and
        the base including an annular or semi-annular ridge configured to position the container relative to the base, the annular or semi-annular protruding wall being positioned outside the annular or semi-annular ridge as seen in a plan view of the base.

11. The holding tool in combination with the device according to claim 10, wherein both the central portion of the base and the central portion of the cover include the opening that permits the state of the liquid or the subject to be viewed.

12. The holding tool in combination with the device according to claim 10, wherein the annular or semi-annular protruding wall comprises a plurality of semi-annular protruding walls that protrude upwardly away from the base.

13. The holding tool in combination with the device according to claim 10, wherein the base includes a groove on a lower surface for preventing the base from sticking to a working surface.

14. The holding tool in combination with the device according to claim 10, further comprising a seal positioned between a portion of the container and a portion of the lid to seal the interior of the device.

15. The holding tool in combination with the device according to claim 10, wherein the container and the lid are made of a light transmissive material.

16. The holding tool in combination with the device according to claim 10, wherein the subject immersed in the liquid is a sheet cell culture.

17. The holding tool in combination with the device according to claim 10, wherein the annular or semi-annular protruding wall comprises a plurality of protruding walls that are spaced apart from one another in a circumferential direction so that a space exists between circumferentially adjacent protruding walls.

18. The holding tool in combination with the device according to claim 10, wherein the annular or semi-annular ridge has a semi-annular shape, the annular or semi-annular protruding wall comprising at least two protruding walls arranged in a semi-annular shape and spaced apart from one another so that a space exists between the two protruding walls, the base including a projection positioned opposite the space between the two protruding walls.

19. A method comprising:
   positioning a device on a base, the device comprising a container and a lid engaged with one another and enclosing an interior, the interior containing a liquid and a subject immersed in the liquid, the base including an annular or semi-annular upstanding wall that projects upwardly away from the base;
   the positioning of the device on the base including positioning the lid relative to the base using the annular or semi-annular upstanding wall;
   engaging a cover with the base while the device is positioned on the base to enclose the device in an interior defined by the base and the cover;
   the engaging of the cover with the base pressing the container and the lid towards each other;
   the cover including a central portion and the base including a central portion, the central portion of the base or the central portion of the cover including an opening that permit viewing of a state of the liquid or the subject in the device; and
   the base including an annular or semi-annular ridge configured to position the container relative to the base, the annular or semi-annular upstanding wall being positioned outside the annular or semi-annular ridge as seen in a plan view of the base.

20. The method according to claim 19, wherein the engaging of the cover with the base includes threadably engaging a portion of the base with a portion of the cover.

21. The method according to claim 19, wherein the subject immersed in the liquid is a sheet cell culture.

22. The method according to claim 19, wherein both the central portion of the base and the central portion of the cover include the opening to permit viewing of a state of the liquid or the subject in the device.

23. The method according to claim 19, wherein the positioning of the device on the base includes positioning the container so that the upstanding ridge surrounds a bottom portion of the container.

24. The method according to claim 19, wherein the annular or semi-annular upstanding wall comprises a plurality of protruding walls.

25. The method according to claim 19, wherein the annular or semi-annular upstanding wall comprises a plurality of protruding walls that are spaced apart from one another in a circumferential direction so that a space exists between circumferentially adjacent protruding walls.

26. The method according to claim 19, wherein the annular or semi-annular ridge has a semi-annular shape, the annular or semi-annular protruding wall comprising at least two protruding walls arranged in a semi-annular shape and spaced apart from one another so that a space exists between the two protruding walls, the base including a projection positioned opposite the space between the two protruding walls, the positioning of the device on the base including sliding the device between the space and the projection.

* * * * *